(12) United States Patent
Furukawa et al.

(10) Patent No.: US 8,193,512 B2
(45) Date of Patent: Jun. 5, 2012

(54) IRRADIATION FIELD FORMING DEVICE

(75) Inventors: Takuji Furukawa, Chiba (JP); Kouji Noda, Chiba (JP)

(73) Assignee: National Institute of Radiological Sciences, Chiba (JP)

( * ) Notice: Subject to any disclaimer, the term of this patent is extended or adjusted under 35 U.S.C. 154(b) by 752 days.

(21) Appl. No.: 11/922,204

(22) PCT Filed: Oct. 31, 2005

(86) PCT No.: PCT/JP2005/019968
§ 371 (c)(1),
(2), (4) Date: Dec. 14, 2007

(87) PCT Pub. No.: WO2006/134677
PCT Pub. Date: Dec. 21, 2006

(65) Prior Publication Data
US 2010/0213384 A1    Aug. 26, 2010

(30) Foreign Application Priority Data
Jun. 15, 2005 (JP) ................................ 2005-175604

(51) Int. Cl.
*G21K 5/10* (2006.01)
(52) U.S. Cl. .................... 250/397; 250/396 R; 250/400; 250/492.1; 600/1; 600/2
(58) Field of Classification Search ............... 250/396 R, 250/397, 398, 400, 396 ML, 431.1, 492.1, 250/492.3, 41.1, 492.19; 600/1, 2
See application file for complete search history.

(56) References Cited

U.S. PATENT DOCUMENTS

| 4,134,017 | A | | 1/1979 | Azam et al. | |
| 5,039,867 | A | * | 8/1991 | Nishihara et al. | 250/492.3 |
| 5,969,367 | A | * | 10/1999 | Hiramoto et al. | 250/492.3 |
| 2002/0033456 | A1 | * | 3/2002 | Tachikawa et al. | 250/398 |
| 2004/0079899 | A1 | * | 4/2004 | Ma | 250/492.3 |
| 2005/0231138 | A1 | * | 10/2005 | Nakanishi et al. | 315/500 |

FOREIGN PATENT DOCUMENTS

| JP | 53-8500 | 1/1978 |
| JP | 8-257148 | 8/1996 |
| JP | 08-229145 | 9/1996 |
| JP | 2001-000562 | 1/2001 |

* cited by examiner

*Primary Examiner* — David A Vanore
*Assistant Examiner* — Nicole Ippolito
(74) *Attorney, Agent, or Firm* — Squire Sanders (US) LLP

(57) ABSTRACT

An irradiation field forming device for forming an irradiation field when a specimen is irradiated with a charged particle beam generated by an accelerator, the irradiation field forming device includes: a range shifter arranged on a beam axis of the charged particle beam for regulating an irradiation depth of the charged particle beam; and two or more than two converging electromagnets arranged in the downstream of the range shifter for regulating a beam diameter of the charged particle beam which is enlarged by the range shifter to a constant value.

4 Claims, 6 Drawing Sheets

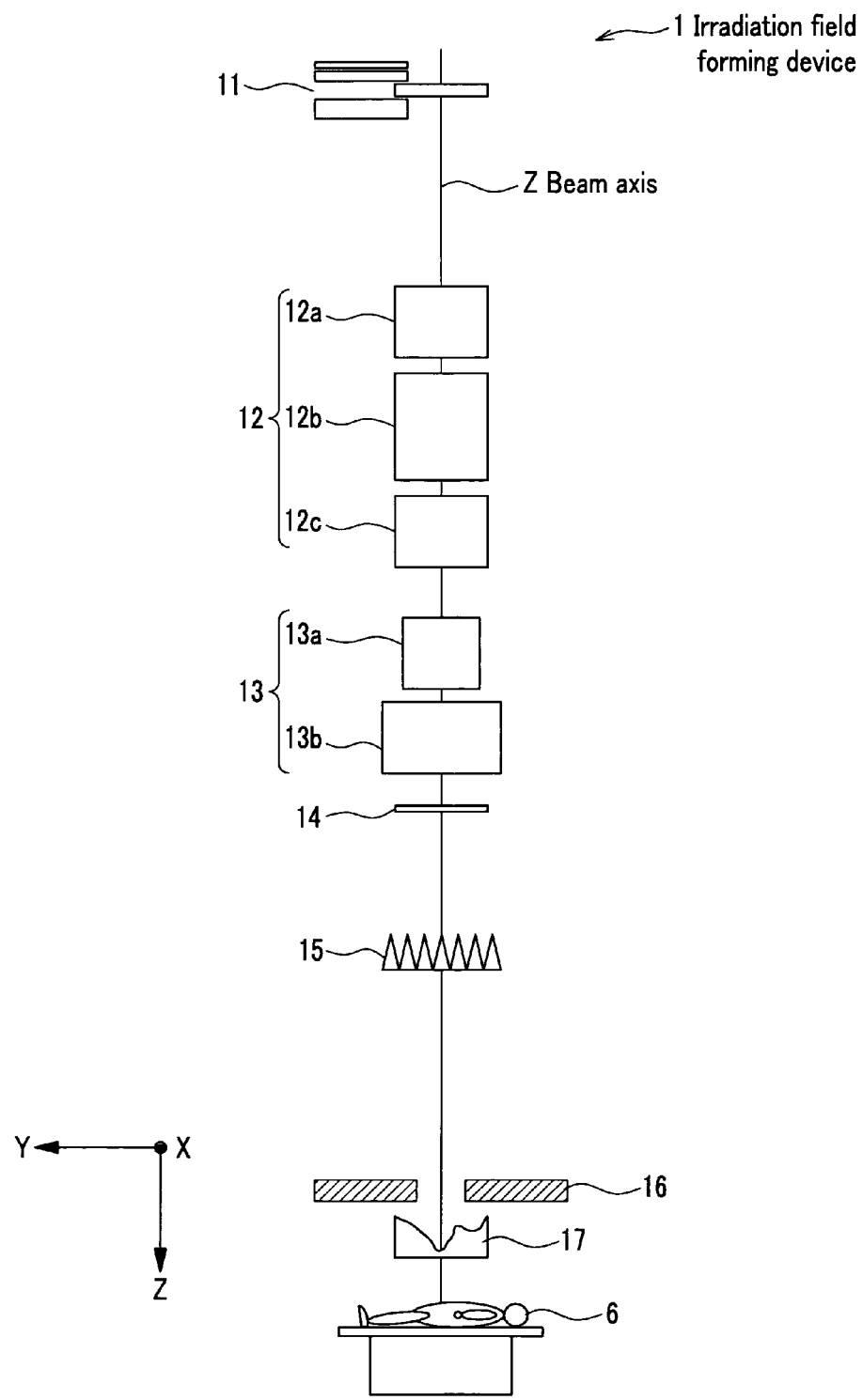

IRRADIATION FIELD FORMING DEVICE

TECHNICAL FIELD

This invention generally relates to an irradiation field forming device for forming an irradiation field of a charged particle beam generated by an accelerator, and more particularly relates to an irradiation field forming device for forming the irradiation field with a constant beam diameter regardless of an irradiation depth.

BACKGROUND ART

In recent years, as a new medical treatment for cancers, a charged particle beam treatment which irradiates a charged particle beam on an affected area of a specimen has been expected. Heavy ions represented by, for example, a proton and a carbon ion are included in charged particles to be used for the medical treatment.

Dose of common radiation ray such as X-ray or γ-ray is high in a portion just under a body surface and gradually decreases according to a depth from the body surface. On the contrary, dose of a charged particle beam is low in a portion close to the body surface and rapidly increases to achieve a peak at a given depth (generally, the peak is called "Bragg peak"), and the charged particle beam does not penetrate beyond the peak. By regulating a position and height of the Bragg peak to irradiate a tumor according to a shape thereof, it becomes possible to take a shot at a cancer lesion.

For generating a charged particle beam, particle are ionized by an ion source and accelerated by an accelerator such as synchrotron by giving energy to the particles. For example, in the case of generating a carbon ion beam, carbon ions are accelerated to a speed 84% of the speed of light in the accelerator. Then, the accelerated charged particle beam is transported through a beam transport channel to irradiate a specimen by an irradiation means.

Generally, a size of an affected area of a specimen is larger than a beam diameter of a charged particle beam generated by an accelerator. Therefore, as a method for uniformly irradiating a whole affected area with the charged particle beam, a method (Wobbler method) that irradiates the affected area with the charged particle beam by enlarging a beam diameter and a method (spot scanning method) that dispersedly irradiates the affected area by three-dimensionally scanning an irradiation spot without enlarging the beam diameter have been used.

In the both methods described above, an irradiation depth of the beam is regulated according to a position and shape of the affected area of a specimen. A regulation of the irradiation depth can be achieved by controlling energy of the charged particle beam.

There are two methods for controlling the energy of the charged particle beam.

One method is to control an energy supplied to the charged particles by controlling an output of the accelerator. However, this method is not easy since there are many components to be controlled in the accelerator, and further, an accurate control is required for each of the components.

The other energy control method is to attenuate the energy of the charged particle beam by setting a material, which is called a range shifter, for absorbing the energy of the charged particle beam on a beam axis (for example, see patent literature 1). The method which uses the range shifter can easily control the energy of the charged particle beam, compared with the method which controls the output of the accelerator.

Patent literature 1: Japanese Patent Laid-open Publication No. 2001-562

However, when the energy of the charged particle beam is controlled by using the range shifter, a beam diameter of the charged particle beam is enlarged along a traveling direction as a secondary effect after passing through the range sifter. That is, the beam diameter is varied depending on an irradiation depth in the specimen. As a result, a treatment planning has been difficult. Especially, in the spot scanning method, three-dimensional filling out of the affected area of the specimen with a uniform irradiation spot becomes difficult.

Therefore, to solve the issue described above, there has been a demand for an irradiation filed forming device which can form an irradiation field with a constant beam diameter, while regulating an irradiation depth of the charged particle beam.

DISCLOSURE OF INVENTION

To solve the above-described issue, in the present invention, there is provided a constitution for controlling an enlargement of the beam diameter by a range shifter, by disposing two or more than two converging electromagnets in the downstream of the range shifter.

According to the present invention, the beam diameter can be maintained constant by the two or more than two converging electromagnets arranged in the downstream of the range shifter, while an irradiation depth of the charged particle beam is regulated by the range shifter.

BRIEF DESCRIPTION OF DRAWINGS

FIG. 6 is a schematic constitutional view of an irradiation filed forming device according to a second embodiment.

PREFERRED MODE(S) FOR CARRYING OUT THE INVENTION

Hereinafter, a best mode (hereinafter, referred to as embodiment) for embodying the present invention will be explained in detail by referring to drawings as needed.

First Embodiment

First, a first embodiment will be explained. The first embodiment is a case of irradiating a specimen with a charged particle beam by the spot scanning method.

Figure 1:
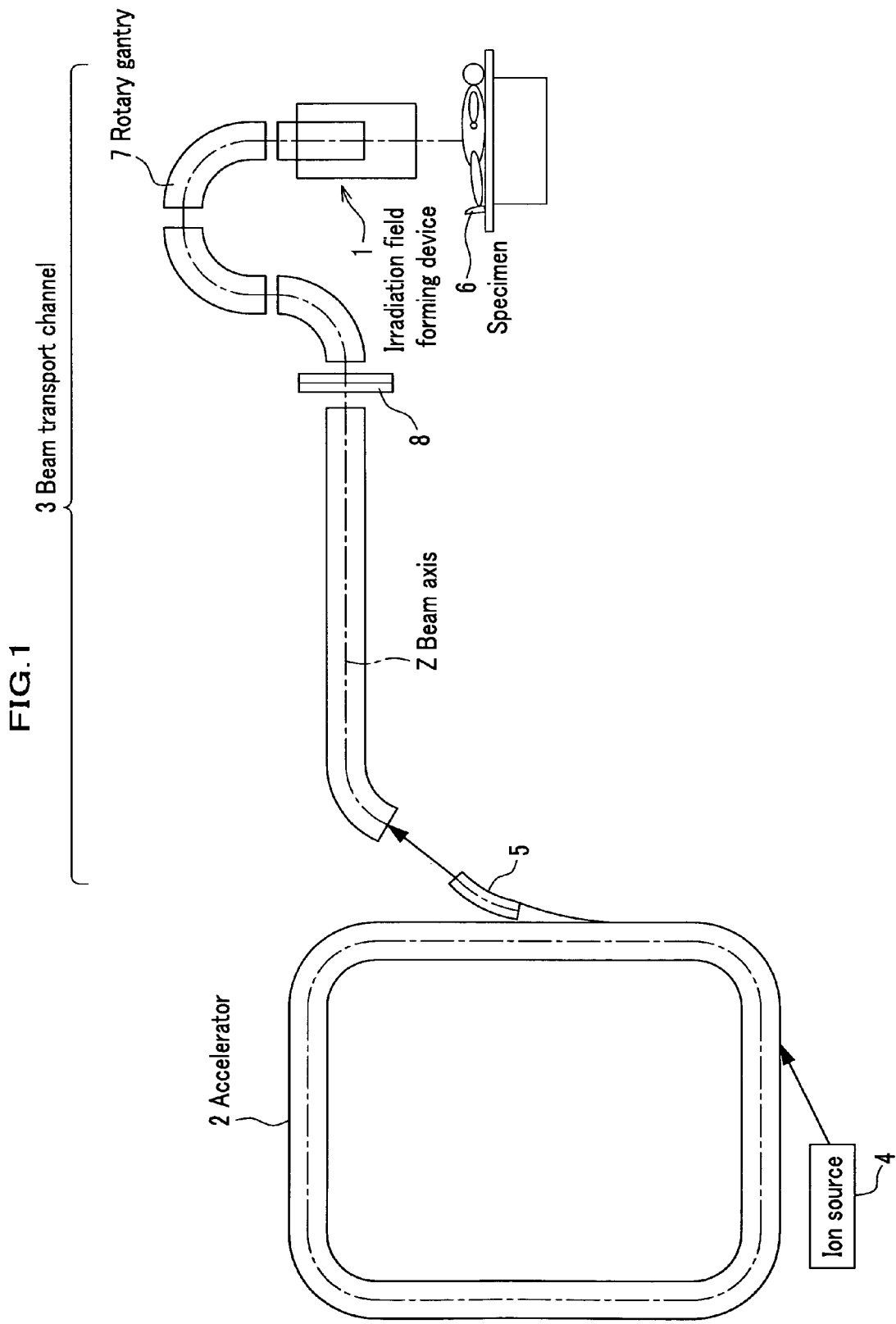
FIG. 1 is a schematic view for explaining a whole constitution of the present embodiments.

FIG. 1 is a schematic view for explaining a whole constitution according to the present embodiment. As shown in FIG. 1, an irradiation field forming device 1 is located in the downstream of a beam transport channel 3 which is capable of communication with an accelerator 2. In FIG. 1, charged particles ionized by an ion source 4 are introduced into the accelerator 2. The accelerator 2 accelerates the charged particles by giving energy to the charged particles, while circulating the charged particles, to generate a charged particle beam (hereinafter, referred to as beam). The generated beam is exit from the accelerator 2 via an exit deflector 5 and reaches the irradiation field forming device 1 through the beam transport channel 3. Next, the irradiation field forming device 1 forms an irradiation field with a constant beam diameter to irradiate a specimen 6, while regulating energy of the beam.

It is noted that a rotary gantry 7 located in the downstream of the beam transport channel 3 is rotatably disposed through a connector 8 and driven by a source of power such as a motor, which is not shown. The irradiation field forming device 1 according to the embodiment is arranged in the downstream of the beam transport channel 3 as described above. However, it is preferable that the arrangement area of the irradiation field forming device 1 is in the rotary gantry 7. By arranging the irradiation field forming device 1 in the rotary gantry 7 as described above, the specimen 6 can be irradiated from various directions using the spot scanning method. Therefore, an irradiation of the beam in response to a cancer having a complex shape and a minimum exposure of a normal area to the charged particle beam can be achieved.

Figure 2:
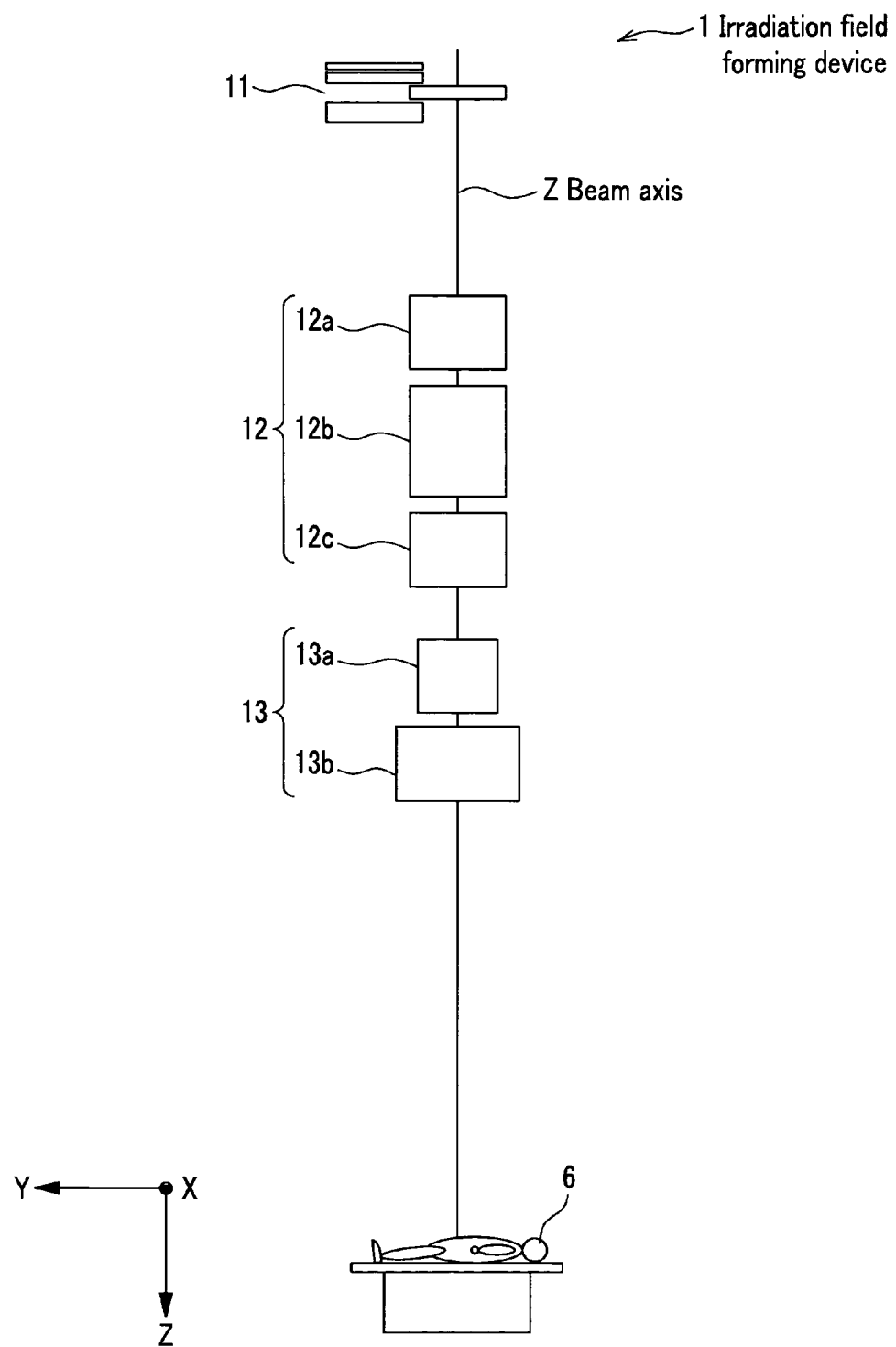
FIG. 2 is a schematic constitutional view of an irradiation field forming device according to a first embodiment.

FIG. 2 is a schematic constitutional view of the irradiation field forming device 1 according to the first embodiment. As shown in FIG. 2, in the irradiation field forming device 1, a range shifter 11, three quadrupole electromagnets 12 for converging the beam, and two deflection electromagnets 13 are sequentially disposed on a beam axis Z along a beam traveling direction.

In addition, these components described above are controlled by a control unit which is common and not shown. For example, the control unit can change a plate thickness of the range shifter 11, and can control a power of a direct current applied to the quadrupole electromagnet 12 according to the plate thickness of the range shifter 11.

It is noted that in the coordinates included in FIG. 2, a Z-axis means the beam axis Z described above and corresponds to a beam orbit when the beam is not deflected by the deflection electromagnet 13. An X-axis is an arbitrary axis perpendicular to the Z-axis and a Y-axis is an axis perpendicular to both the Z-axis and X-axis.

The range shifter 11 is used for attenuating an energy of the beam by absorbing the energy of the beam. The range shifter 11 is generally composed of a plurality of plates which have different thicknesses and a plate thickness can be selected depending on a desired irradiation depth of the beam. A material of the range shifter 11 may be any substance, for example, metals, plastics, and ceramics as long as the substance attenuates the energy of the beam. Usually, an acrylic plate is used for the range shifter 11. In addition, by installing a driving means, which is not shown, such as an air cylinder in the range shirt 11, the plate can automatically be exchanged by transmitting a signal from a control unit.

The irradiation depth of the beam can be regulated by changing a thickness of the range shifter 11 as described above, thereby controlling an attenuation amount of the beam energy. That is, in the coordinates shown in FIG. 2, the irradiation depth of the beam in the Z-axis direction can be determined by the range shifter 11.

Then, the beam passed through the range shifter 11 reaches the quadrupole electromagnet 12 which is arranged in the downstream of the range shifter 11. At this time, the thicker the thickness of the range sifter 11 is, the more the energy of the beam is attenuated, while a diameter of the beam is enlarged.

The quadrupole electromagnet 12 includes two quadrupole electromagnets 12a, 12c for converging the beam in the X-direction and one quadrupole electromagnet 12b for converging the beam in the Y-direction.

A deflection electromagnet 13 includes two dipole electromagnets 13a, 13b for forming two magnetic fields which are mutually orthogonal and used for deflecting the beam orbit in the X-direction and Y-direction, respectively. That is, in the coordinates shown in FIG. 2, the irradiation spot of the beam in the X-direction and Y-direction can be determined by the deflection electromagnet 13.

Figure 3:
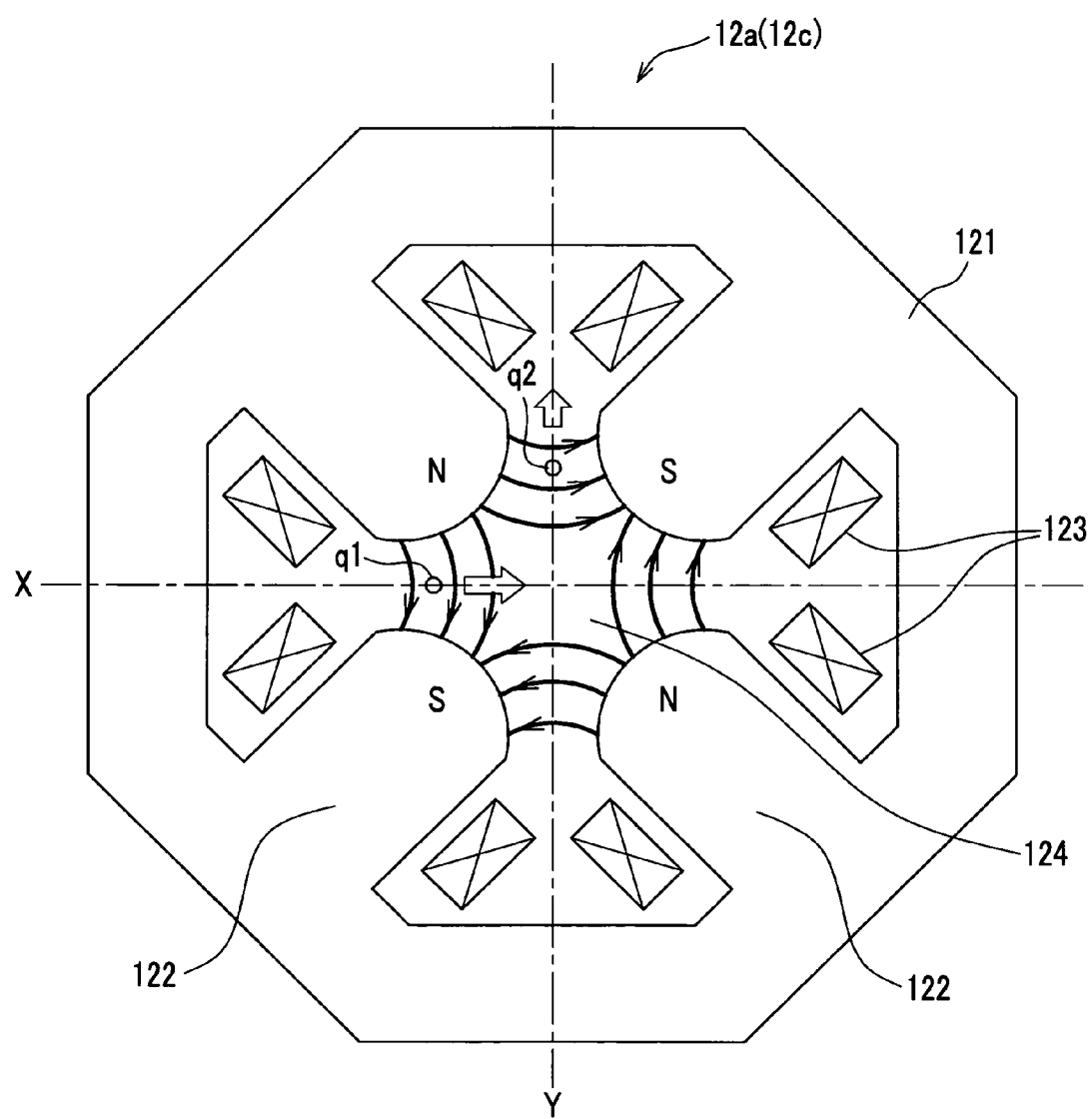
FIG. 3 is a cross sectional view of a quadrupole electromagnet 12a taken along a plane (X-Y plane) perpendicular to a beam axis Z.

Here, a structure of the quadrupole electromagnet 12a (or 12c) for converging the beam in the X-direction will be explained in detail by referring to FIG. 3. FIG. 3 is a cross sectional view of the quadrupole electromagnet 12a taken along a plane (X-Y plane) perpendicular to the beam axis Z. As shown in FIG. 3, the quadrupole electromagnet 12a includes a magnetic yoke 121 which has substantially a ring shape, four magnetic cores 122 which are protruded inward from the magnetic yoke at an equal angle each other among the four magnetic cores 122, and a magnetizing coil 123 wound separately on each of the magnetic cores 122, and a magnetic field shown with solid line arrows is generated in a gap 124 inside the yoke 121.

By the quadrupole electromagnet 12a described above, a Lorentz force works, for example, on a charged particle located at q1 on the X-axis in the inward direction. On the other hand, for example, with respect to a charged particle located at q2 on the Y-axis, the Lorentz force works on the particle in the outward direction. That is, the quadrupole electromagnets 12a, 12c converges the beam in the X-axis direction, while diverging the beam in the Y-direction.

In addition, the quadrupole electromagnet 12b which converges the beam in the Y-axis direction can be constituted by reversing a direction of the direct current applied to the magnetizing coil 123 of the quadrupole electromagnet 12a. Specifically, if the direct current applied to the magnetizing coil 123 is reversed, a direction of the magnetic field generated in the gap 124 is reversed, thereby the directions of the converging and diverging (direction of Lorentz force applied to charged particle is also reversed) are also reversed. That is, the quadrupole electromagnet 12b converges the beam in the Y-axis direction, while diverging the beam in the X-direction.

In addition, strengths for converging and diverging the beam by the quadrupole electromagnet 12 can be controlled by the intensity of the direct current applied to the quadrupole electromagnet 12.

<Spot Scanning Method>

Figure 4:
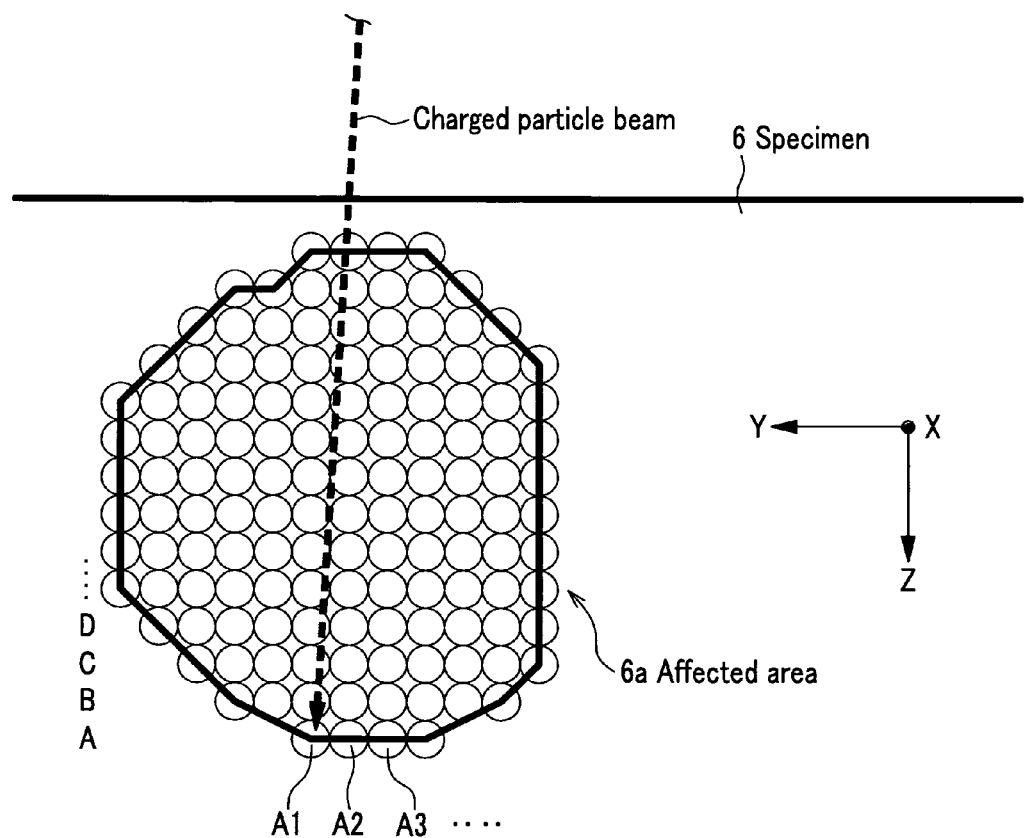
FIG. 4 is a schematic view for explaining an example to scan an irradiation spot on an affected area of a specimen in the spot scanning method.

Next, a spot scanning method according to the embodiment will be explained using FIG. 4, while referring to FIG. 1 and FIG. 2. FIG. 4 is a schematic view for explaining an example to scan an irradiation spot on an affected area of a specimen in the spot scanning method.

First, as shown in FIG. 1, an exit beam from the accelerator 2 reaches the irradiation field forming device 1 located at an end of the beam transport channel 3 through the beam transport channel 3. In this case, a plate thickness of the range shifter 11 of the irradiation field forming device 1 shown in FIG. 2 is changed in advance according to a desired irradiation depth.

Next, energy of the beam to be reached to the irradiation field forming device 1 is attenuated by the range shifter 11 of the irradiation field forming device 1 shown in FIG. 2 to regulate the irradiation depth, while the beam diameter is enlarged.

Then, the beam whose diameter is enlarged by the range shifter 11 is regulated by the quadrupole electromagnet 12 in a constant beam diameter at a desired irradiation depth.

Next, an irradiation spot of the beam, whose diameter is regulated to be constant by the quadrupole electromagnet 12, is determined by the deflection electromagnet 13 which deflects the beam orbit in the X-direction and Y-direction.

By the procedure described above, as shown in FIG. 4, first, one irradiation spot A1 within an affected area 6a can be irradiated with the beam.

Then, by controlling the deflection electromagnet 13, a whole plane A within the affected area 6a is irradiated with the beam by sequentially displacing the irradiation spot as A2, A3, ..., .

When the irradiation on the plane A in the affected area 6a is completed, the irradiation depth is changed by regulating a thickness of the range shifter 11. For example, in FIG. 4, a dispersed irradiation of the beam on a plane B in the affected area 6a is started. In this case, the direct current applied to the quadrupole electromagnet 12 is controlled according to the thickness of the range shifter 11 so that the plane B is irradiated with a beam diameter identical to that of the plane A.

In addition, according to a similar procedure described above, all planes such as plane C, plane D, ..., in the affected area 6a can be sequentially irradiated with the dispersed irradiation to complete an entire irradiation of the whole affected area 6a.

Here, a procedure for regulating a beam diameter to be constant by the three quadrupole electromagnets according to the embodiment will be explained by referring to FIG. 5.

Figure 5:
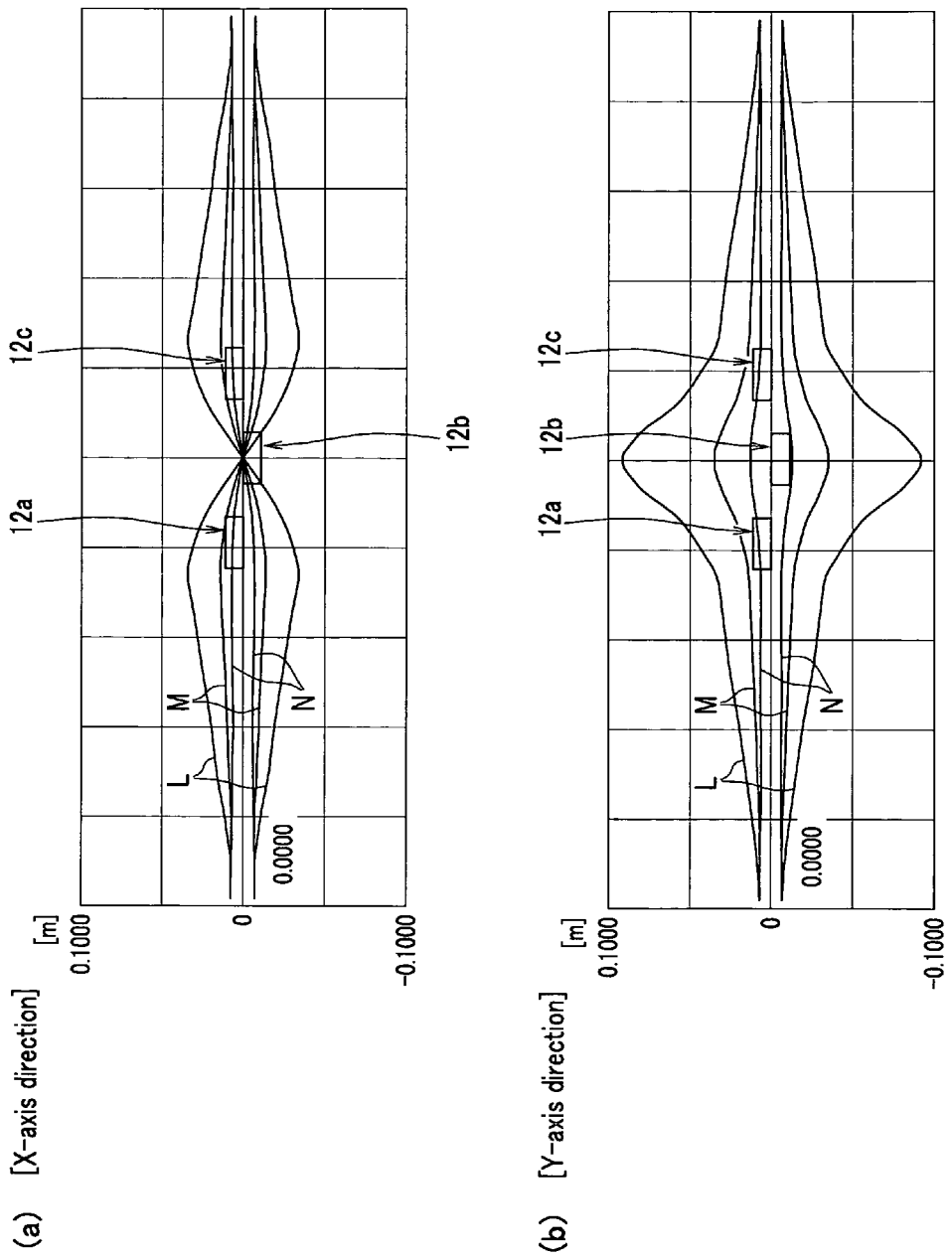
FIG. 5 is a figure for explaining a beam orbit which is constantly regulated by three quadrupole electromagnets 12 according to the present embodiments.

FIG. 5 is a figure for explaining a beam orbit which is constantly regulated by the three quadrupole electromagnets 12 according to the embodiment, and (a) shows beam orbits in the X-axis direction and (b) shows beam orbits in the Y-axis direction. In addition, in each of FIGS. 5 (a), (b), the range shifter 11 is arranged at a left end and three beam orbits L, M, and N, which are enlarged by the range shifter 11 in three patterns corresponding to each of three thicknesses of the range shifter 11, are shown.

It is noted that in FIG. 5, the three quadrupole electromagnets 12 are disposed to be perpendicular to the beam axis Z and mirror symmetrical with respect to a plane passing through a center of the quadrupole electromagnet 12b. By arranging two or more than two quadrupole electromagnets 12 to be mirror symmetrical, a calculation of the orbit may be simplified in some cases.

In addition, in the control unit which is not shown, a value of the direct current to be applied to each of the quadrupole electromagnets 12 according to a thickness of the range shifter 11 is stored. The value of the direct current can be calculated in advance by calculating the orbit.

First, the beam is enlarged in the X-axis direction and Y-axis direction by passing through the range shifter 11, and reaches the quadrupole electromagnet 12a.

A direct current is applied to the quadrupole electromagnet 12a for largely converging a component in the X-axis direction of the beam which is enlarged by the range shifter 11, while a component in the Y-axis direction of the beam is enlarged.

Therefore, for compensating the component in the Y-axis direction of the beam enlarged by the quadrupole electromagnet 12a, a direct current is applied to the quadrupole electromagnet 12b so as to converge the component in the Y-axis direction, while the component in the X-axis direction of the beam is enlarged.

Then, a direct current is applied to the quadrupole electromagnet 12c so that each of the components in the X-axis direction and Y-axis direction becomes a predetermined value.

As described above, by controlling a balance of the conversing and diverging among the quadrupole electromagnets 12a to 12c, the beam diameter can be regulated to a constant value.

In addition, as shown by the beam orbits L, M, and N in FIG. 5, the beam diameter can be regulated to a constant value even if a thickness of the range shifter is varied.

As described above, in the spot scanning method according to the present embodiment, a conventional issue in which a beam diameter is varied depending on an irradiation depth can be solved. As a result, the affected area 6a of the specimen 6 can be three-dimensionally irradiated with the charged particle beam whose diameter is regulated to be constant.

Second Embodiment

Next, a second embodiment will be explained. The second embodiment is a case that the specimen 6 is irradiated with a charged particle beam by a Wobbler method. It is noted that in explanations of the second embodiment, a duplicated explanation with the first embodiment described above will be omitted.

FIG. 6 is a schematic constitutional view of an irradiation filed forming device 1 according to the second embodiment. As shown in FIG. 6, in the irradiation field forming device 1, the range shifter 11, three quadrupole electromagnets 12 for converging the beam, two deflection electromagnets 13, a scatterer 14, a ridge filter 15, a collimator 16, and a bolus 17 are sequentially disposed on the beam axis Z of the charged particle beam along a beam traveling direction.

The scatterer 14 is made of, for example, aluminum, tantalum, and lead and scatters the beam to enlarge a diameter of the beam with which the specimen 6 is irradiated.

The ridge filter 15 expands an energy distribution in a beam traveling direction. The ridge filter 15 may be a constitution composed of a metal plate having, for example, a step-like thickness. Due to passing of the beam through the ridge filter 15, the Bragg peak is enlarged to expand a medical treatment area per one irradiation in the beam axis Z direction.

The collimator 16 limits an irradiation area of the beam, with which the specimen 6 is irradiated, on a plane (X-Y plane) perpendicular to the beam axis Z according to a shape of the affected area 6a.

The bolus 17 limits an irradiation area of the beam, with which the specimen 6 is irradiated, in the beam axis Z direction according to a shape of the affected area 6a.

<Wobbler Method>

Next, a Wobbler method according to the present embodiment will be explained by referring to FIG. 6.

In FIG. 6, since processes until the beam reaches the deflection electromagnet 13 are identical to those of the spot scanning method described above, explanations of the processes will be omitted.

The beam is controlled to draw a circular pattern by the deflection electromagnet 13 which deflects a beam orbit in the X-axis direction and Y-axis direction. By controlling the beam as described above, a large and uniform irradiation field can be formed when the specimen 6 is irradiated with the beam.

When the beam reaches the scatterer 14, the beam diameter is enlarged through the scattering.

Here, a difference of the beam diameter to be enlarged by the range shifter 11 and the scatterer 14 will be clarified. Since a beam diameter enlarged by the range shifter 11 varies depending on a thickness of the range shifter 11, it is necessary that the beam diameter is regulated to a constant diameter by the quadrupole electromagnet 12.

On the other hand, since an incident beam into the scatterer 14 is regulated to a constant diameter by the quadrupole electromagnet 12, the beam diameter enlarged by the scatterer 14 maintains a constant diameter even after the beam is scattered by the scatterer 14. That is, it is unnecessary to regulate the beam diameter after the beam passed the scatterer 14.

Subsequently, the Bragg peak of the beam is enlarged by the ridge filter 15 and reaches the collimator 16.

Then, an irradiation area of the beam is limited by the collimator 16 and bolus 17 according to a shape of the affected area 6a, and the specimen 6 is irradiated with the beam.

As understood from the explanation described above, in the Wobbler method, the irradiation depth is regulated by the range shifter 11 and bolus 17. Therefore, if the irradiation depth is deep a thin range shifter 11 is used, and if the irradiation depth is shallow a thick range shifter 11 is used. As described above, since a thickness of the range shifter 11 is changed depending on the irradiation depth, a size of the irradiation field to be finally formed is also changed in the conventional Wobbler method.

However, in the Wobbler method according to the present embodiment, the conventional issue that a beam diameter varies depending on an irradiation depth has been solved. As a result, regardless of a depth of the affected area 6a of the specimen 6, the affected area 6a of the specimen 6 can be irradiated with a beam regulated to a constant beam diameter according to a shape of the affected area 6a of the specimen 6.

<<Others>>

It is noted that the present invention is not limited to the above-described embodiments.

In the embodiments, the explanation of the irradiation field forming device 1 has been made by defining an order of a position of each of the components in the total arrangement. However, in the irradiation field forming device 1, the order of the position of each of the components may be changed as needed as long as the quadrupole electromagnet 12 is disposed in the downstream of the range shifter 11.

In addition, in the embodiments, the three quadrupole electromagnets 12 has been used for converging a beam diameter. However, the beam diameter can be properly regulated to a constant beam diameter if a constitution of the irradiation field forming device 1 includes at least one electromagnet for converging the beam in the X-axis direction and at least one electromagnet for converging the beam in the Y-axis direction. In addition, an order of these quadrupole electromagnets 12 is also not limited.

In addition, in the embodiments, the quadrupole electromagnet 12 is used for converging a beam diameter. However, a multi-pole electromagnet having six-poles or more than six-poles may also be used. For example, the six-pole electromagnet includes a magnetic yoke having substantially a ring shape, six magnetic cores protruded inward from the magnetic yoke at an equal angle each other among the six magnetic cores, and a magnetizing coil wound separately on each of the magnetic cores. By using the multi-pole electromagnet having six-poles or more than six-poles, an advantage capable of compensating energy aberrations of the beam in inward and outward directions is obtained, in addition to the converging effect of the beam diameter by the quadrupole electromagnet.

In addition, it is unnecessary that the two or more than two converging electromagnets are identical such that the electromagnets are quadrupole only or the six-poles only. If the irradiation field forming device 1 includes two or more than two electromagnets having four poles or more than four poles, the beam diameter can be regulated to a constant beam diameter.

In addition, in the embodiments, the explanation has been made using an example in which the irradiation field forming device 1 is applied to the rotary gantry 7. However, the irradiation field forming device 1 may be applied to an irradiation device which does not use the rotary gantry 7.

The invention claimed is:

1. An irradiation field forming device configured to form an irradiation field when a specimen is irradiated with a charged particle beam generated by an accelerator, the irradiation field forming device comprising:
   a range shifter, disposed on a beam axis of the charged particle beam, configured to regulate an irradiation depth of the charged particle beam;
   at least two converging electromagnets, disposed in a downstream of the range shifter, configured to regulate a beam diameter of the charged particle beam, which is enlarged by the range shifter, to a constant value;
   two deflection electromagnets disposed downstream of the at least two converging electromagnets, wherein the two deflection electromagnets are configured to form two magnetic fields that are mutually orthogonal and used to deflect a beam orbit in the X-direction and Y-direction, respectively; and
   a control unit configured to change a plate thickness of the range shifter and to control a power of a direct current applied to the at least two converging electromagnets according to the plate thickness of the range shifter.

2. The irradiation field forming device according to claim 1,
   wherein the at least two converging electromagnets comprise a quadrupole electromagnet.

3. The irradiation field forming device according to claim 1,
   wherein the at least two converging electromagnets comprise a multipole electromagnet.

4. A rotary gantry comprising the irradiation field forming device according to claim 1.

* * * * *